United States Patent [19]

Matsumoto et al.

[11] Patent Number: 4,793,339

[45] Date of Patent: Dec. 27, 1988

[54] ULTRASONIC ATOMIZER AND STORAGE BOTTLE AND NOZZLE THEREFOR

[75] Inventors: Kazuhiro Matsumoto; Kei Asai; Hirohito Yamamoto, all of Nagaokakyo, Japan

[73] Assignee: Omron Tateisi Electronics Co., Shimokaiinji, Nagaokakyo-City, Kyoto, Japan

[21] Appl. No.: 153,467

[22] Filed: Feb. 4, 1988

Related U.S. Application Data

[63] Continuation of Ser. No. 770,078, Aug. 28, 1985, abandoned.

[30] Foreign Application Priority Data

| | | | |
|---|---|---|---|
| Aug. 29, 1984 | [JP] | Japan | 59-181453 |
| Sep. 7, 1984 | [JP] | Japan | 59-136282 |
| Sep. 8, 1984 | [JP] | Japan | 59-136310 |
| Sep. 10, 1984 | [JP] | Japan | 59-190153 |
| Sep. 12, 1984 | [JP] | Japan | 59-192269 |

[51] Int. Cl.[4] .................. A61M 11/00

[52] U.S. Cl. .................. 128/200.16; 141/31; 222/566; 222/571; 239/338

[58] Field of Search .................. 128/200.14, 200.16; 222/563, 566, 571; 239/102.2, 338, 553.5; 141/31, 382

[56] References Cited

U.S. PATENT DOCUMENTS

| | | | |
|---|---|---|---|
| 1,728,203 | 2/1915 | Weichel | 141/31 |
| 2,057,745 | 10/1936 | Scheyer et al. | 222/571 |
| 2,067,554 | 1/1937 | Vahle | 141/382 |
| 2,241,840 | 5/1941 | Achtziger | 222/571 |
| 3,032,276 | 5/1962 | Brainard | 128/200.14 |
| 3,199,510 | 8/1965 | Sinai | 128/200.14 |
| 3,746,000 | 7/1973 | Edwards | 128/200.16 |
| 3,806,100 | 4/1974 | Cornett | 128/200.16 |
| 4,119,096 | 10/1978 | Drews | 128/200.16 |
| 4,301,093 | 11/1981 | Eck | 128/200.16 |
| 4,544,004 | 10/1985 | Fitter et al. | 141/31 |

FOREIGN PATENT DOCUMENTS

| | | | |
|---|---|---|---|
| 2637162 | 5/1978 | Fed. Rep. of Germany . | |
| 3236831 | 5/1983 | Fed. Rep. of Germany . | |
| 352708 | 7/1931 | United Kingdom | 222/571 |

*Primary Examiner*—Edward M. Coven
*Assistant Examiner*—Randy Citrin
*Attorney, Agent, or Firm*—Wegner & Bretschneider

[57] ABSTRACT

This ultrasonic atomizer includes an oscillating member, a means for vibrating the oscillating member at a supersonic frequency, a bottle for liquid storage, with an opening, fitted generally above the oscillating member with regard to the preferred orientation of the atomizer during use, and a nozzle fitted into the opening of the bottle, this nozzle having a tip portion protruding outside the bottle in the generally downwards direction and approached closely to the oscillating member. The nozzle is formed with a fine groove for leading liquid in the bottle downwards to the tip portion of the nozzle by capillary action and by gravitational action, and with an aperture for introducing air from the outside into the bottle. Thereby liquid in the bottle may be properly supplied to the oscillating member to be atomized in a controlled fashion, and interruption of liquid supply and also dribbling of liquid are positively prevented. Constructions for the nozzle and for the bottle are also disclosed.

17 Claims, 9 Drawing Sheets

ULTRASONIC ATOMIZER AND STORAGE BOTTLE AND NOZZLE THEREFOR

This application is a continuation of U.S. application Ser. No. 770,078, filed Aug. 28, 1985 now abandoned.

BACKGROUND OF THE INVENTION

The present invention relates to the field of ultrasonic atomizing inhalers, and in particular to an improved ultrasonic atomizing inhaler, and a nozzle and a liquid storage bottle therefor, which improve on the prior art.

There are various types of ultrasonic atomizing inhalers; one of these typically has a horn construction for vibrating at an ultrasonic frequency and for atomizing liquid supplied thereto, and the atomized liquid drifts away from said horn construction and enters into the mouth and/or the nose of a user. Such an ultrasonic atomizing inhaler is typically used for the inhalation of liquid medicine, and for humidification of the larynx of the user.

A typical such ultrasonic atomizing inhaler is shown in FIG. 1 of the accompanying drawings in sectional view. In this inhaler, the cone shaped horn construction d serves for concentrating ultrasound waves from its larger end to vibrate the oscillating plate e fixed at its smaller end. A supply c of liquid such as medicine is held in the storage bottle b, and is picked up therefrom by a wick construction a and is delivered little by little to the oscillating plate e by capillary action, whence it is atomized into the air as described above. Thus, the wick construction a is made from an absorbent material with a fine network or filamentary structure such as cotton, and raises a flow of the liquid c in the bottle b upwards by capillary action from the lower end of said wick construction a dipped in said liquid c to deliver said liquid flow to the oscillating plate e at the top end of said wick construction a.

In such a conventional ultrasonic atomizing inhaler, since the bottle b is provided below the oscillating plate e, the supply of the liquid b is solely dependent upon the effect of capillary action in the wick construction a which in fact is fighting against the action of gravity upon said liquid b, and especially when the liquid b is rather viscous satisfactory supply thereof may no occur properly. This causes unsatisfactory atomization action. Furthermore, the proper supply of liquid from the bottle b to the oscillating plate e is rather dependent upon the level of liquid in the bottle b, and when the amount of liquid remaining in said bottle b becomes little the change of level required to be provided by the capillary action is all the greater. As a result, it is difficult to properly atomize the last portion of the liquid c in the bottle b. This can be very troublesome, particularly if the liquid is an expensive medicinal liquid.

It might be conceived of to place the bottle b at a higher level, but then it would be likely that oversupply of liquid through the wick construction a would occur. This could in the worst case cause troublesome dribbling down of the liquid, and attendant waste and mess. Again, in the case that the liquid were an expensive medicinal liquid, this would be quite unacceptable.

Now, another problem that can occur with the shown prior art is that the wick construction a, after being kept impregnated with water or medicinal liquid for some time, may start to breed bacteria, or may start to emit a bad odor; this is very unhygenic. Further, since when refilling the ultrasonic atomizing inhaler, typically the wick construction a is replaced in order partially to avoid these problems, the device is not economical in use, and is wasteful of materials. Further, if the viscosity of the liquid to be atomized is great, such a transport mechanism as the wick construction a cannot effectively supply it to the oscillating plate e.

Also, when refilling the ultrasonic atomizing inhaler, it is typically necessary to remove the wick construction or its analog part. However, this can be very troublesome, and can lead to wear on the inhaler or on the fitting parts thereof. Further, the likelihood can develop of loss or damage to some small and fiddly part which is required to be removed and replaced, and further a possibility arises of improper refitting of said part.

SUMMARY OF THE INVENTION

Accordingly, it is the primary object of the present invention to provide an ultrasonic atomizer which overcomes the above outlined problems.

It is a further object of the present invention to provide such an ultrasonic atomizer which effects proper supply of liquid to be atomized.

It is a further object of the present invention to provide such an ultrasonic atomizer which does not cause oversupply of liquid to be atomized.

It is a further object of the present invention to provide such an ultrasonic atomizer which does not cause undersupply of liquid to be atomized.

It is a further object of the present invention to provide such an ultrasonic atomizer which can satisfactorily supply for atomization the last dregs of the quantity of liquid to be atomized.

It is a yet further object of the present invention to provide such an ultrasonic atomizer which can satisfactorily supply even viscous liquid.

It is a yet further object of the present invention to provide such an ultrasonic atomizer which is not wasteful of atomization liquid.

It is a yet further object of the present invention to provide such an ultrasonic atomizer which is not wasteful of other supplies.

It is a yet further object of the present invention to provide such an ultrasonic atomizer which is not uneconomical during use.

It is a yet further object of the present invention to provide such an ultrasonic atomizer which is not prone to dribbling of atomization liquid.

It is a yet further object of the present invention to provide such an ultrasonic atomizer which is not liable to cause a mess.

It is a yet further object of the present invention to provide such an ultrasonic atomizer which is economical to manufacture.

It is a yet further object of the present invention to provide such an ultrasonic atomizer which does not require any high dimensional accuracy during manufacture.

It is a yet further object of the present invention to provide such an ultrasonic atomizer which is not prone to quick wearing out.

It is a yet further object of the present invention to provide such an ultrasonic atomizer which can be easily replenished.

It is a yet further object of the present invention to provide such an ultrasonic atomizer which can be replenished without removal of any small or fiddly part thereof.

It is a yet further object of the present invention to provide such an ultrasonic atomizer which is not prone to loss of any such small or fiddly part.

It is a yet further object of the present invention to provide such an ultrasonic atomizer which is not prone to misassembly.

It is a yet further object of the present invention to provide such an ultrasonic atomizer which can be easily cleaned.

It is a yet further object of the present invention to provide a nozzle, and a bottle, for an ultrasonic atomizer, which in themselves serve for attaining at least some of the above described objects.

According to the most general aspect of the present invention, these and other objects are accomplished by an ultrasonic atomizer comprising: (a) an oscillating member; (b) a means for vibrating said oscillating member at a supersonic frequency; (c) a bottle for liquid storage, with an opening, fitted generally above said oscillating member with regard to the preferred orientation of said atomizer during use; and (d) a nozzle fitted into said opening of said bottle, comprising a tip portion protruding outside said bottle in the generally downwards direction and approached closely to said oscillating member; (e) said nozzle being formed with a fine groove for leading liquid in said bottle downwards to said tip portion of said nozzle by capillary action and gravitational action, and with an aperture for introducing air from the outside into said bottle.

According to such a structure, the flow of the liquid to be atomized is in the generally downwards direction, and thus is aided both by the effect of gravity and also of capillary action in the fine liquid leading groove. As liquid is progressively thus removed from the bottle and is atomized at the oscillating member, air is introduced into the bottle by an amount of approximately the same volume as the removed liquid, and accordingly the pressure in the bottle remains approximately at atmospheric pressure, and no undesirable suction effect occurs. Thereby, there is provided an ultrasonic atomizer which effects proper supply of liquid to be atomized, which does not cause oversupply or undersupply of liquid to be atomized, and which further can satisfactorily supply for atomization the last dregs of the quantity of liquid to be atomized. This ultrasonic atomizer can satisfactorily supply even viscous liquid, and is not wasteful of atomization liquid, or of other supplies, since there is no requirement to change any wick like construction, and the nozzle can simply be cleaned. Thus, this ultrasonic atomizer is not uneconomical during use. Further, it is not prone to dribbling of atomization liquid, and thus is not liable to cause a mess.

Further, according to a more particular aspect of the present invention, these and other objects are more particularly and concretely accomplished by an ultrasonic atomizer as described above, further comprising a tube member fitted between said nozzle and said opening of said bottle; and said tube member may be elastic, and may be in the radially compressed state as fitted between said nozzle and said opening of said bottle. This construction provides a good sealing effect, even if the internal surface of the opening of the bottle and the external surface of the nozzle fitting thereinto are somewhat rough, and accordingly this feature means that the ultrasonic atomizer does not require any high dimensional accuracy during manufacture, accordingly is economical to manufacture, and further is not prone to quick wearing out. And this tube member may serve for partly delimiting the aforementioned liquid supply groove, which is effective for aiding with the capillary action and for promoting dimensional accuracy, which improves accuracy of liquid supply. Further, this ultrasonic atomizer, because the nozzle can be easily dismounted, can be easily cleaned.

Further, according to a yet more particular aspect of the present invention, these and other objects are yet more particularly and concretely accomplished by an ultrasonic atomizer as described above, wherein the portion of said bottle remote from said opening thereof is flexible—or, in its entirety, said bottle may be formed from a flexible substance.

According to such a structure, it is easy to supply liquid into this bottle, by dipping the tip of the liquid supply nozzle into the liquid, and by pinching the upper part of the bottle which is made of the soft material by the fingers and by releasing it thereafter. Thus, the liquid is introduced into the bottle by a syringe effect. Accordingly, there is provided an ultrasonic atomizer which can be easily replenished, without removal of any small or fiddly part thereof. Thus, this ultrasonic atomizer is not prone to loss of any such small or fiddly part, or to misassembly after being refilled.

Further, according to a yet more particular aspect of the present invention, these and other objects are yet more particularly and concretely accomplished by an ultrasonic atomizer as described above, wherein said bottle is formed with a filling opening proximate to said opening thereof in which said nozzle is fitted. This opening may advantageously be used for refilling said bottle, without necessarily removing the bottle from the ultrasonic atomizer, after inverting said atomizer from its preferred orientation for use. This can be very convenient.

BRIEF DESCRIPTION OF THE DRAWINGS

The present invention will now be shown and described with reference to the preferred embodiments thereof, and with reference to the illustrative drawings. It should be clearly understood, however, that the description of the embodiments, and the drawings, are all of them given purely for the purposes of explanation and exemplification only, and are none of them intended to be limitative of the scope of the present invention in any way, since the scope of the present invention is to be defined solely by the legitimate and proper scope of the appended claims. In the drawings, like parts and spaces and so on are denoted by like reference symbols in the various figures thereof; in the description, spatial terms are to be everywhere understood in terms of the relevant figure; and:

DESCRIPTION OF THE PREFERRED EMBODIMENTS

Figure 1:
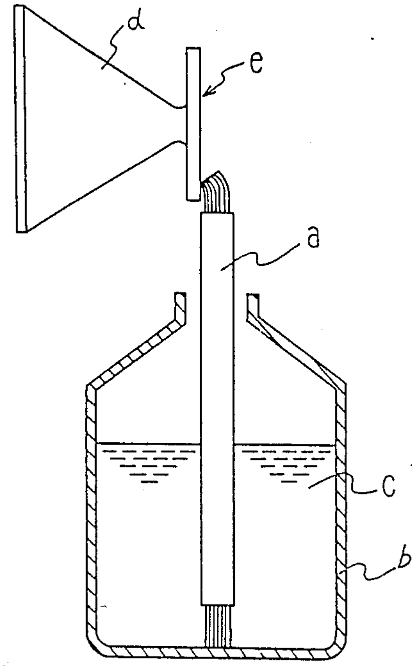
FIG. 1 PRIOR ART
FIG. 1 is a longitudinal sectional view of a conventional ultrasonic inhaler.
Figure 2:
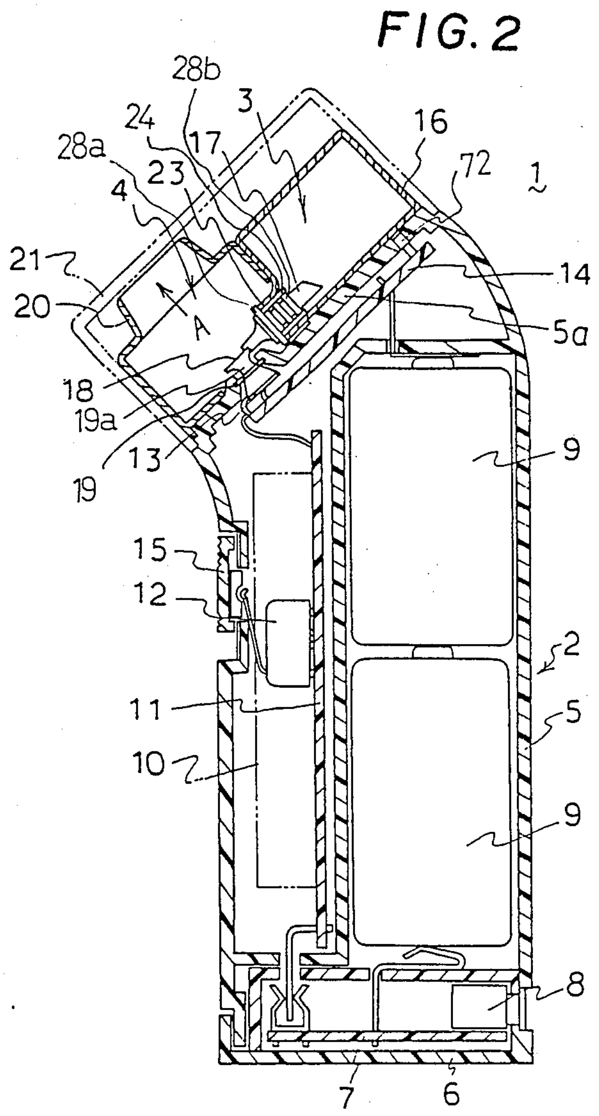
FIG. 2 is a longitudinal sectional view of the first preferred embodiment of the ultrasonic inhaler of the present invention.

The present invention will now be described with reference to the preferred embodiments thereof, and with reference to the appended drawings. FIG. 2 is a longitudinal sectional view of the first preferred embodiment of the ultrasonic inhaler of the present invention, which incorporates the first preferred embodiments of the storage bottle and of the atomizer nozzle of the present invention. In this figure, the reference numeral 1 generally denotes the ultrasonic inhaler, and this is made up of a main body 2, a liquid supply assembly 3, and an inhalation unit 4.

The main body 2 defines the external contour of the ultrasonic inhaler, and comprises a main body casing 5 an a bottom plate 6. In the main body casing 5 there are housed a pair of batteries 9, 9 in a battery receiving portion thereof, and a power plug 8 with a power source circuit board 7 is further held below said batteries 9, 9. The bottom plate 6 serves for closing the bottom of the main body casing 5 and for retaining the batteries 9, 9 and the power plug 8 therein. An oscillation circuit board 11 is fitted parallel to the batteries 9, 9 at one side thereof, and bears an electronic circuit unit 10 including for example an oscillation circuit. A micro switch 12 is provided for controlling the apparatus, and is covered by a slidable switch cover 15. And a drive circuit board 14 is provided at the top end of the main body 5, just below a top wall portion 5*a* thereof, for driving an oscillation element 13.

On the other side of the top wall portion 5*a* are provided the liquid supply assembly 3 and the inhalation unit 4. When the ultrasonic inhaler is not in use, a hygienic cap 21, shown in FIG. 2 by double dotted lines only, covers both these assemblies. The liquid supply assembly 3, which will be discussed in greater detail later, comprises a storage bottle 16 for containing water or liquid medication and a liquid supply nozzle 17 fitted into said storage bottle 16 for allowing the controlled removal of liquid therefrom to the inhalation unit 4. The inhalation unit 4 comprises an inhalation nozzle 20 adapted to be approached to the nose and mouth of a user, and a horn unit 19 which has an oscillating atomization plate 18 integrally formed at the small end of a rigid cone shaped portion 19*a* and an ultrasonic oscillation element 13 fitted at the larger end of said rigid cone shaped portion 19*a*. The main body casing 5, the bottom plate 6, the switch cover 15, and the hygienic cap 21 are made of a material such as ABS resin, while the storage bottle 16, the liquid supply nozzle 17, and the inhalation nozzle 20 are made of a material such as styrene resin.

In detail, the horn unit 19 is mounted at the lower portion of the top wall portion 5*a* of the main body casing 5 of the ultrasonic inhaler, with the ultrasonic oscillating element 13 on the inside and the oscillating atomization plate 18 facing outwards, and the inhalation nozzle 20 is detachably mounted to said top wall portion 5*a* over said horn unit 19 with its opening confronting the oscillating plate 18 and facing outwards. And the storage bottle 16 is detachably mounted at the upper portion of the top wall portion 5*a*, with the liquid supply nozzle 17 fitted thereinto substantially positioned at the lowest point thereof, and with the lower end of said liquid supply nozzle 17 positioned very close to the oscillating atomization plate 18 as will be explained hereinafter in detail. A LED (light emitting diode) 72 is provided as fitted through the top wall body portion 5*a*, and is illuminated when the ultrasonic inhaler 1 is operating: the storage bottle 16 is desirably made of transparent or translucent material, so that said LED 72 can be observed from the outside of the ultrasonic inhaler, when the hygienic cap 21 is removed, to monitor the action of the ultrasonic inhaler. When the storage bottle 16 has liquid such as medicine contained therein, this liquid may create a certain lens effect, to amplify the visibility of the LED 72; in any case, if this liquid is colored, it will modify the color of the light emitted by said LED 72.

Thus, when it is desired to use this ultrasonic inhaler 1, first the user—who has, as will be more particularly explained later in this specification, previously filled the storage bottle 16 with liquid such as water or medicine which is to be atomized and inhaled—removes the hygienic cap 21, and, after approaching his or her mouth and nose near the opening of the inhalation nozzle 20, switches ON the microswitch 12 by pushing appropriately on the switch cover 15. Thereby, the oscillation circuit of the electronic circuit unit 10 drives the ultrasonic oscillating element 13 of the horn unit 19 to oscillate at an ultrasonic frequency, and this causes the atomization plate 18 to similarly oscillate with a considerable amplitude, due to the amplifying effect provided by the rigid cone shaped portion 19*a*. As will be explained shortly, a controlled supply of the liquid in the storage bottle 16 is provided to this atomization plate 18, and thus the vibration at ultrasonic frequency of the oscillation plate 18 atomizes this liquid into very minute droplets, which drift away from the atomization plate 18 in the direction indicated by the arrow A in FIGS. 2 and 6 through the inhalation nozzle 20 to enter the mouth and nose of the user of the ultrasonic inhaler 1, as desired.

Figure 3:
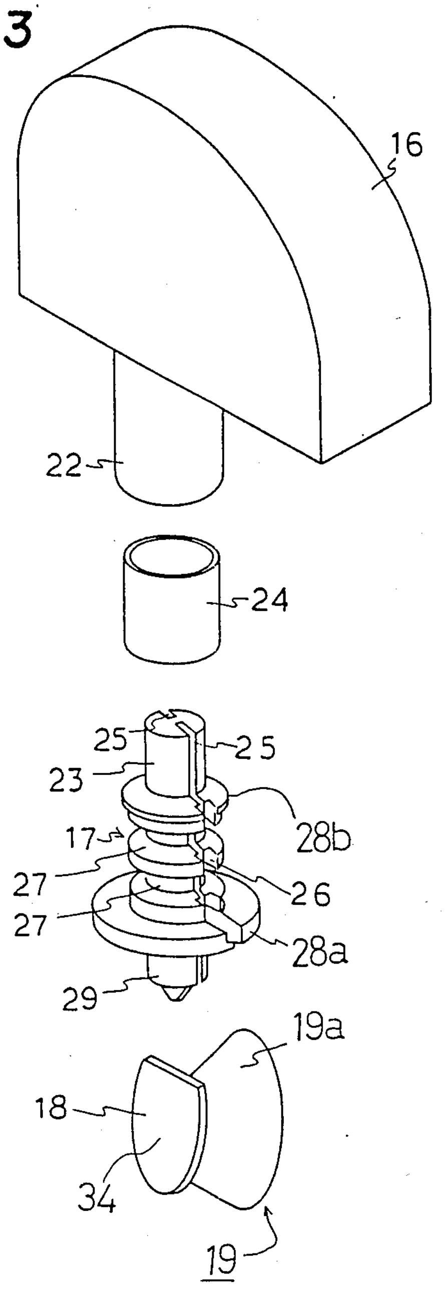
FIG. 3 is an exploded perspective view showing a liquid storage bottle, a liquid supply nozzle for fitting thereinto, and a horn atomization unit of the FIG. 2 ultrasonic inhaler.
Figure 4:
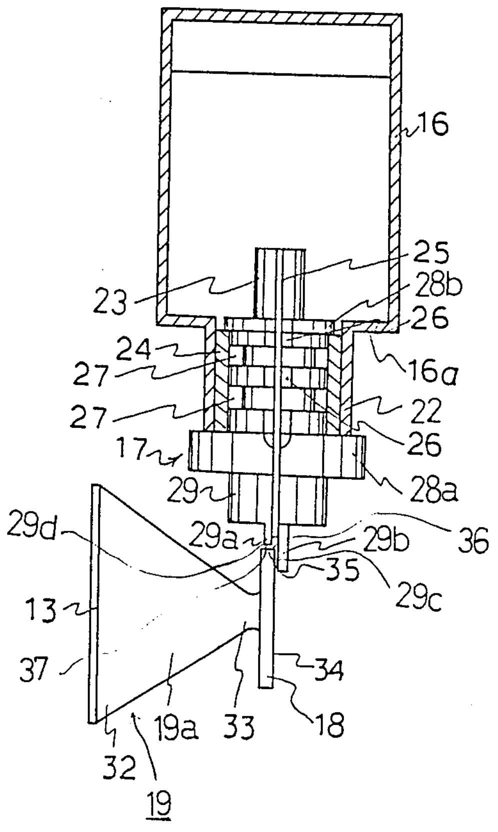
FIG. 4 is a sectional view showing said bottle, said nozzle as fitted thereinto, and said horn unit properly positioned with respect thereto, as seen from the side.
Figure 5:
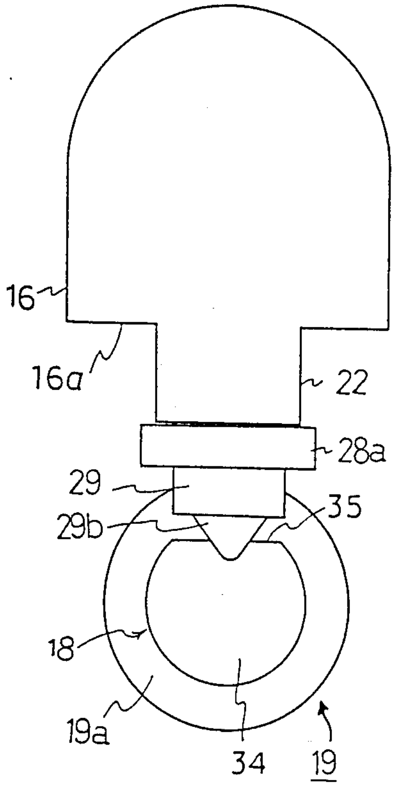
FIG. 5 is a view of these parts as seen from the right side in FIG. 4, in the same position.

Now, the detailed construction of the storage bottle 16, the liquid supply nozzle 17, and the horn unit 19 will be explained, with reference to FIGS. 3 through 6. In FIG. 3, there is shown an exploded perspective view of these parts, with the liquid supply nozzle 17 removed from the bottle 16; while FIG. 4 is a sectional view of the bottle 16, the nozzle 17 fitted thereinto, and the horn unit 19 as seen from the side, and FIG. 5 is a view of these parts as seen from the right side in FIG. 4. Further, FIG. 6 shows these parts as fitted to the top wall portion 5*a* of the main body casing 5.

Figure 6:
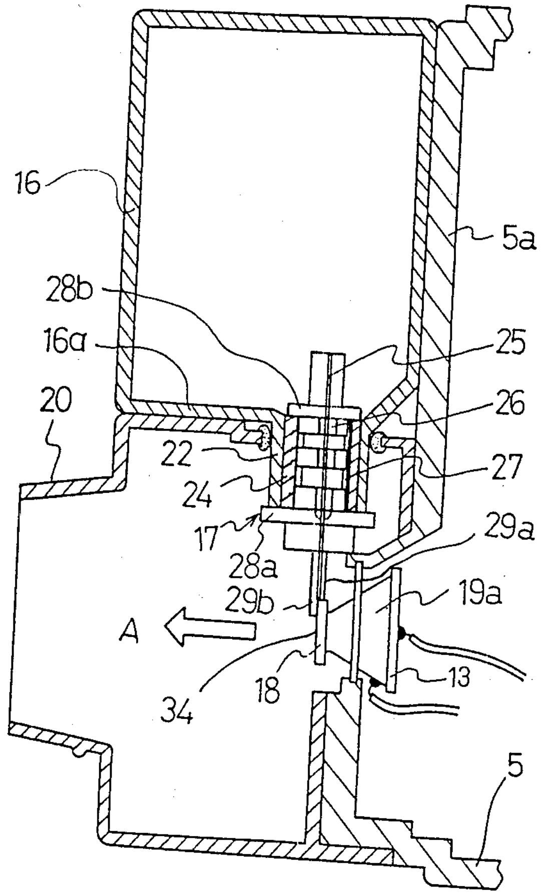
FIG. 6 shows these parts as fitted to the top wall portion of the main body casing of the ultrasonic inhaler of FIG. 2.

The storage bottle 16 is shaped, in this first preferred embodiment, in an inverted U shape as seen from the front, as in FIG. 5, and further is shaped in a rectangular shape as seen from the side, as in FIGS. 4 and 6. As previously mentioned, the bottle 16 is formed from a transparent or translucent styrene resin. And from the bottom surface 16*a* of the storage bottle 16 there projects a tubular nozzle fitting member 22.

Into this tubular nozzle fitting member 22 there is fitted the aforementioned liquid supply nozzle 17, with the interposition therebetween of a tube 24 made of a rubber like elastic material. This tube 24 is required to be somewhat distended, in order to be fitted over the nozzle 17, and further is then required to be somewhat compressed, in order for the nozzle 17 with said tube 24 fitted thereover to be fitted into the nozzle fitting member 22; accordingly, when this fitting has been accomplished, the inner cylindrical surface of the tube 24 is closely and sealingly contacted to the portions of the outer surface of the nozzle 17 with which it is in contact, and the outer cylindrical surface of said tube 24 is similarly closely and sealingly contacted to the inner cylindrical surface of the tubular nozzle fitting member 22. And thereby the nozzle 17 is securely held in said nozzle fitting member 22.

The form of the liquid supply nozzle 17 will now be explained. This nozzle 17 has a generally cylindrical shape, with a flange 28*a* formed near its one end 29 which is outside the storage bottle 16 and another smaller flange 28*b* formed near its other end 23 which is inside said storage bottle 16. The tube 24 is fitted between these two flanges 28*a* and 28*b* and is axially retained between them. And the larger lower flange 28*a* further serves for locating the nozzle 17 relative to the bottle 16, when said nozzle is fitted into the tubular nozzle fitting member 22 of said bottle 16. A plurality of circumferential grooves 27 (two in the shown construction) are formed as extending round the portion of the nozzle 17 between said two flanges 28*a* and 28*b*, and a pair of liquid supply grooves 25 extending in the longitudinal direction of the nozzle 17, thus being orthogonal to the circumferential grooves 27, and spaced diametrically opposite from one another around said nozzle 17, are formed as cut quite deeply into the material of said nozzle 17; these liquid supply grooves 25 are extremely fine, for proper obtaining of capillary action as will be explained hereinafter, and function for leading liquid from the interior of the storage bottle 16 to the atomization plate 18. The circumferential grooves 27 are provided for forming temporary storage reservoirs for fluid which is being taken out from the storage bottle 16 through the liquid supply grooves 25, as will be explained in greater detail later. And through the two flanges 28*a* and 28*b* and through the flange portions remaining between on either side of the grooves 27 there are cut, superimposed upon the outer portion of the liquid supply grooves 25 and wider than said liquid supply grooves 25, two air supply grooves 26; these air supply grooves 26 are substantially wider than the liquid supply grooves 25, and function for leading air from the outside to the interior of the storage bottle 16. The end 23 of the liquid supply nozzle 17 inside the storage bottle 16 is quite long, and has the continued end portion of the liquid supply grooves 25 formed on it, thus appropriately leading said liquid supply grooves well into the liquid inside said bottle 16. And, as best seen in the sectional view of FIG. 4, the lower end 29 of the liquid supply nozzle 17 is formed with two projecting end portions 29*a* and 29*b* separated by the two liquid supply grooves 25: the longer projecting end portion 29*b* is substantially longer than the other portion 29*a*, being formed in a substantially triangular shape, and its inside surface 29*d* is substantially planar; while the shorter projecting end portion 29*a* is cut off straight, having a substantially straight downwardly facing edge 29*c*.

The horn unit 1 comprises the rigid cone shaped portion 19*a*, and at the larger end of said portion 19*a* is fitted the per se known ultrasonic oscillation element 13. At the smaller end of said rigid cone shaped portion 19*a* there is integrally formed the oscillating atomization plate 18, in an orientation perpendicular to the axis of said cone shape thereof; and this atomization plate 18 is formed as a disk with a portion thereof defined by a chord 35 cut away. Thus, the surface 34 of the plate 18 facing away from the cone shaped portion 19*a* is substantially planar. As best shown in FIG. 4, the horn unit 19 is so mounted to the top wall portion 5*a* of the main body casing 5, relative to the storage bottle 16, that this surface 34 of said atomization plate 18 confronts the aforementioned substantially planar inside surface 29*d* of the longer projecting lower end portion 29*b* of the liquid supply nozzle 17 with a certain very narrow gap 36 being defined therebetween. And, moreover, in this position the edge of the plate 18 defined by the chord 35 confronts the flat lower edge 29*c* of the shorter projecting end portion 29*a* of the liquid supply nozzle 17 with another very narrow gap 37 being defined therebetween.

Thus, when the ultrasonic inhaler 1 as described above is being used, with the atomization plate 18 vibrating at ultrasonic frequency as explained above, liquid in the storage bottle 16 passes by the action of gravity and also by capillary action from the interior of said bottle 16, into the upper ends of the liquid supply grooves 25 where they are formed in the inwardly projecting portion 23 of the nozzle 17, and down through these grooves 25. The two circumferential grooves 27 define intermediate fluid reservoirs along this fluid flow path, said reservoirs being communicated to the sides of the grooves 25 at intermediate points therealong. Then the liquid flows to the outside of the bottle 16 down through the portions of the liquid supply grooves 25 formed in the outwardly projecting portion 29 of the nozzle 17, and therefrom flows to the surfaces 29*c* and 29*d* of the projecting end portions 29*a* and 29*b* from which it flows across the narrow gaps 37 and 36 respectively, to the surface 34 of the atomization plate 18. Then, as described previously, this liquid is atomized by the vibration at ultrasonic frequency of said atomization plate 18, and drifts away from said plate 18 to pass through the aperture of the inhalation nozzle 20 to enter the mouth and nose of the user of the ultrasonic inhaler 1. Meanwhile, an amount of air substantially equal in volume to the amount of fluid thus taken out from the bottle 16 enters into the interior of said bottle 16 through the two air supply grooves 26. And since a relatively large volume of liquid may be satisfactorily supplied by the action of gravitation and by capillary action through the two liquid supply grooves 25, and since further reservoirs of liquid en route are provided by the circumferential grooves 27, this supply of liquid to be atomized is performed smoothly and efficiently, according to the amount required, an interruption of liquid supply is never likely to occur. And, since by the shown construction for the ultrasonic inhaler and for the nozzle 17 not only capillary action is relied upon for performing liquid supply but also gravitational action is utilized, there is no problem in supplying for atomization even the last few drops of the liquid contained in the bottle 16, which accordingly may satisfactorily be drained to its uttermost dregs.

However, when the ultrasonic inhaler 1 is switched off, with the atomization plate 18 not vibrating, then by the action of the surface tension of the liquid in the storage bottle 16 no undue supply of liquid from the bottle 16 can occur, and no improper dribbling of liquid can occur. This is further properly ensured by arranging that the liquid supply grooves 25 and the air supply grooves 26, as well as the circumferential grooves 27, are of appropriate dimensions in view of the surface tension and the viscosity, as well as possibly other characteristics, of the type of liquids to be used for atomization.

Now, when it is desired to replenish the storage bottle 16 with liquid, then (referring to FIG. 2) the user removes the hygienic cap 21 and the inhalation nozzle 20 in the upward and leftward direction, and then pulls said storage bottle 16 in the upward and rightward direction along the top wall portion 5*a* of the main body casing 5, and then inverts said bottle 16 so that the liquid supply nozzle 17 is uppermost. Then he or she grips the liquid supply nozzle 17 by its larger retaining flange 28*a* and pulls it out of the bottle 16, along with the tube 24 which naturally remains on said nozzle 17 between the two retaining flanges 28*a* and 28*b* thereof. Then, the user can replenish the storage bottle 16 with fresh liquid for atomization through the aperture of the tubular nozzle fitting member 22 of said bottle 16, or can wash, rinse, etc. said bottle 66 via said aperture. If so deemed desirable, as for purposes of hygiene or the like, at this time the tube portion 24 can be removed from the nozzle 17 and both can be washed and/or sterilized; and then the tube portion 24 is refitted on the end portion of said nozzle 17 by being somewhat stretched out and then by being fitted over it between the flange portions 28*a* and 28*b*, then being allowed to contract so as to fit around the nozzle 17 and so as to perfectly define the upper sides of the groove portions 25, 26, and 27. Afterwards, said user then refits the liquid supply nozzle 17 into said aperture of said nozzle fitting member 22 by forcibly pushing it thereinto, thereby squeezing the sealing tube member 24 and compressing it in the radial direction: and thus a good seal between the nozzle 17 and the nozzle fitting member 22 is assured. Finally, the user refits the replenished storage bottle 16 to the ultrasonic inhaler 1 by inverting said bottle 16 so that the liquid supply nozzle 17 is pointing downwards and by pushing said storage bottle 16 in the downward and leftward direction (as seen in FIG. 2) along the top wall portion 5*a* of the main body casing 5; the storage bottle 16 is then retained in the position shown in FIG. 2 by a clipping arrangement, per se conventional, not shown in the figures. Thus, once again the outwardly projecting portion 29 of the nozzle 17 is closely approached to the atomization plate 18, i.e. the surfaces 29*c* and 29*d* of the projecting end portions 29*a* and 29*b* thereof are so positioned as to again define the narrow gaps 37 and 36 between themselves and the surface 34 of said atomization plate 18; and the ultrasonic inhaler 1 is ready to be used again.

Thus, it is seen that, according to the ultrasonic atomizer of this invention, since the nozzle fitting opening 22 of the storage bottle 16 receives the liquid supply nozzle 17 with the tube 24 being interposed therebetween, an intimate contact is maintained between the liquid supply nozzle 17 and the inner circumferential surface of said nozzle fitting opening 22 of the storage bottle 16, and not only is liquid leakage from said storage bottle 16 prevented, but also the grooves 25, 26, and 27 of the liquid supply nozzle 17 are definitely defined, thereby achieving proper liquid supply. Furthermore, since by the simple action of inserting the single and simple tube 24 said tube 24 makes up for any dimensional roughness between the nozzle fitting opening 22 and the liquid supply nozzle 17, no great care is necessary for the surface finish of the inner surface of the nozzle fitting opening 22 and the liquid supply nozzle 17, as would be required if no such tube as the tube 24 were utilized, so that an economical ultrasonic atomizer may be provided. This is all the more important because the liquid supply nozzle 17 is frequently detached from the storage bottle 16 for cleaning and for resupply of liquid to be atomized, and the provision of the tube 24 prevents any leakage developing at the contact portion between these two members.

Further, it is seen that, according to the ultrasonic atomizer of this invention, inhalation liquids of various viscosity levels can be smoothly and efficiently atomized by properly selecting the widths and the depths of the grooves 25, 26, and 27. And since the liquid supply nozzle 17 may be made of metal or heat resistant resin and the like, and can be removed as explained above and can be boiled, the same nozzle 17 may be used as many times as desired.

Figure 7:
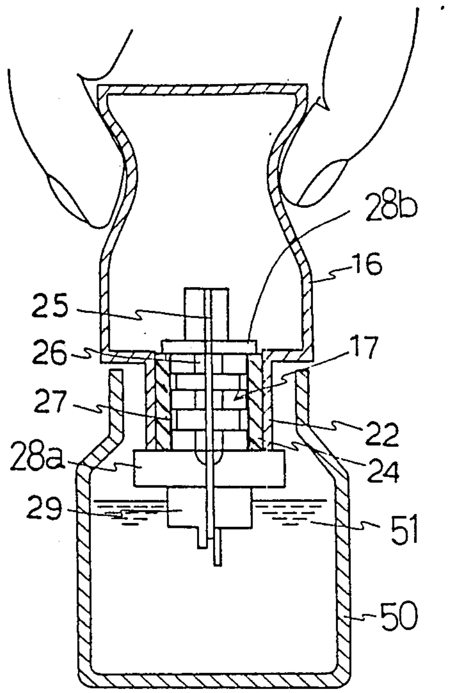
FIG. 7 is a sectional view showing one method of replenishing of the liquid storage bottle shown in FIGS. 2 through 6.

Now, an alternative method of replenishing the storage bottle 16 is illustrated in FIG. 7. According to this method, after the bottle 66 has been removed from the main body 5 of the ultrasonic inhaler 1 as explained above, since in this first preferred embodiment of the present invention said storage bottle 16 is made of a flexible material such as styrene resin, first the user pinches together the front and rear side walls of the upper portion of the bottle 16 (i.e., the part thereof remote from the liquid supply nozzle 17) by using his or her fingers, and then he or she approaches the bottle 16 and the nozzle 17 to an opened bottle 50 containing a fresh supply 51 of liquid for atomization, and plunges the exposed end of the nozzle 17, i.e. the outwardly projecting portion 29 thereof, below the surface of said liquid supply 51. Then the user releases the pinching of the bottle 16, and this causes a suction effect as will easily be understood due to the elasticity of said bottle 16, and thereby a fresh supply of the liquid to be atomized is sucked up into the bottle 16 through the liquid supply grooves 25 in the reverse flow direction to that utilized when the ultrasonic inhaler 1 is being used.

Although in the shown first preferred embodiment of the present invention the entire storage bottle 16 was made of flexible and elastic material such as styrene resin, actually for practicing this rapid and convenient refilling procedure only the upper portion of said storage bottle 16, i.e. the part thereof remote from the liquid supply nozzle 17, need thus be made elastic so as to be pinchable by the fingers of the user.

This method of replenishing the storage bottle 16 is very convenient, because by employing it there is no need to remove the liquid supply nozzle 17 from said storage bottle 16. And, as well as saving a considerable amount of trouble, this means that there is no risk of improper refitting of the liquid supply nozzle 17 into the storage bottle 16, and accordingly reliability is improved. Further, there is no chance of said liquid supply nozzle 17 becoming misplaced, lost, or damaged. Moreover, since when replenishing the storage bottle 16 in this way there is no need for the user to touch any portion of the apparatus which is in contact with the liquid to be atomized (such as the nozzle 17), this means that the ultrasonic inhaler 1 can be used in a very hygienic fashion.

Now, a further alternative method of replenishing the storage bottle 16 will be outlined. In the case of liquid for atomization and inhalation which is sealed into a bottle made of glass or the like by the maker of the medication, by adapting the shape of said bottle made of glass or the like so that the liquid supply nozzle 17 may be directly inserted into said bottle this bottle may be used as the storage bottle 16 of this invention, thus providing a portable, convenient, and hygienic inhaler.

Figure 8:
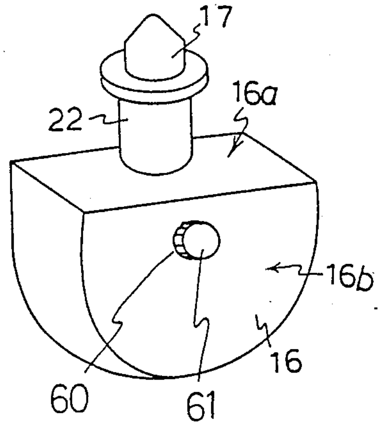
FIG. 8 is a perspective view showing another variant of the liquid storage bottle, in a second preferred embodiment of the present invention.

Now, in FIG. 8, there is shown the liquid storage bottle 16 of a second preferred embodiment of the present invention, which is for being fitted to an ultrasonic inhaler which is otherwise similar to the ultrasonic inhaler illustrated in FIG. 2 and described hereinabove, in an orientation upside down in relation to the orientation illustrated in FIG. 8. In this figure, parts which correspond to parts of the first preferred embodiment shown in FIGS. 2 through 7 and discussed above, and which have the same functions, are denoted by the same reference symbols.

This storage bottle 16 has a hole 60 for replenishing of liquid formed in its bottom surface 16*a*, and a plug 61 made of an elastic material with an H shaped cross section is fitted into said hole 60. In this second preferred embodiment, the hole 60 and the plug 61 are provided in the side surface 16*b* of the storage bottle 16.

Figure 10:
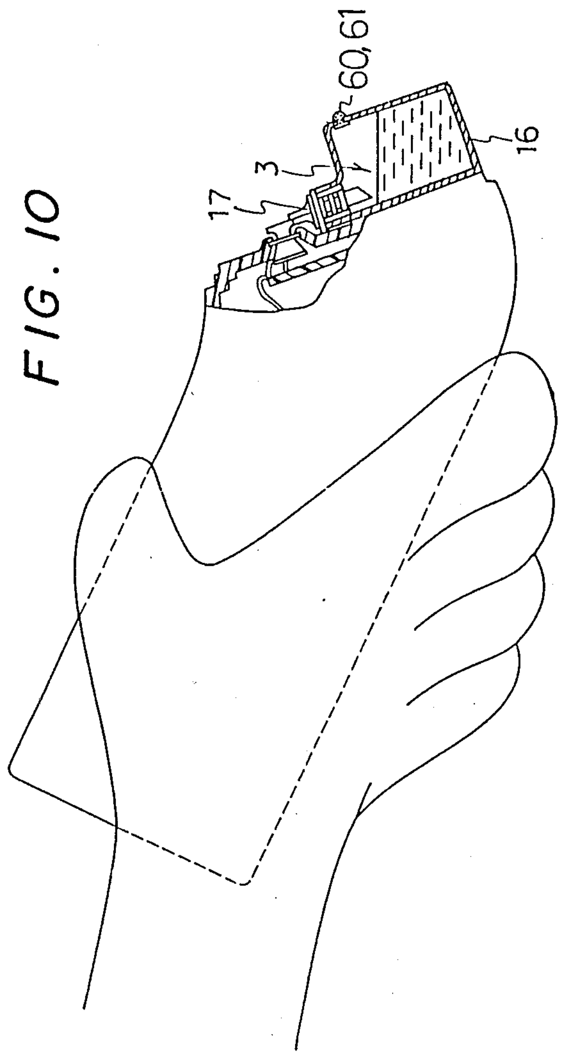
FIG. 10 is a view of the hand of a user holding an ultrasonic inhaler incorporating the liquid storage bottle of FIG. 8 in a position suitable for refilling said liquid storage bottle.

When liquid for being atomized and inhaled is to be freshly supplied into the storage bottle 16, or when such liquid is to be replenished into the storage bottle 16 in an ultrasonic inhaler having the above described structure, the main body portion 5 of the ultrasonic inhaler 1, with the the hygienic cap 21 and optionally with the inhalation nozzle 20 removed, is held by the user by hand with the liquid supply unit 3 in inverted orientation as shown in FIG. 10, namely with the liquid supply nozzle 17 located at an upper position while the storage bottle 16 is located in a lower position. As a result, the liquid supply hole 60 is located above the level of the remaining liquid in the storage bottle 16 and liquid may be supplied into the bottle by removing the plug 61 from the liquid supply hole 60 and by inserting the tip of a syringe or the tip of a glass bottle into said liquid supply hole 60.

By doing so, in this second preferred embodiment, without removing the liquid supply unit 3 from the main body casing 5 of the ultrasonic inhaler 1, liquid may be supplied into the storage bottle 16, and this is extremely convenient. However, it is also possible, with the liquid supply unit 3 removed as shown in FIG. 8, to remove the plug 61 and to supply liquid from the liquid supply hole 60.

Figure 9:
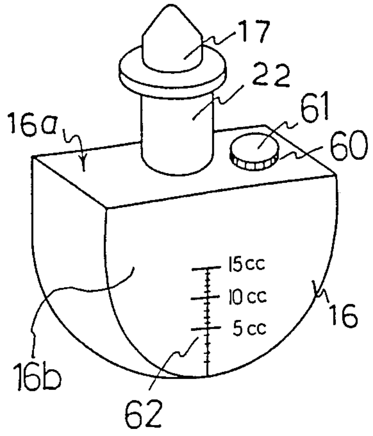
FIG. 9 is a perspective view showing another variant of the liquid storage bottle, in a third preferred embodiment of the present invention.

Although in the above described second preferred embodiment of the present invention the liquid supply hole 60 is provided in the side surface 16*b* of the bottle 16, it is also possible to provide this liquid supply hole 60 having the plug 61 in the bottom surface 16*a* of the bottle 16 near to the nozzle fitting opening 22, and this is the configuration of the third preferred embodiment of the present invention shown in FIG. 9.

It is somewhat more difficult to supply liquid for being atomized and inhaled when this storage bottle 16 having the liquid supply nozzle 17 is fitted into the main body casing 5 of the ultrasonic inhaler 1 as shown in FIG. 10, if the inhalation nozzle 20 is not removed, but, once said inhalation nozzle 20 is removed, in the same manner as that shown in FIG. 10, it is possible to supply liquid into the storage bottle 16 through the liquid supply hole 60, i.e. through the top of the bottle 16. Of course, if the liquid supply unit 3 is removed, it is possible to supply liquid for being atomized and inhaled without any problem.

Also, in this third preferred embodiment, a graduated scale 62 is provided on the side wall 16*b* of the storage bottle 16. In this case, with the liquid supply nozzle 17 facing upward, since the storage bottle 16 is as mentioned above made of transparent resin, it is possible to know to what amount the liquid has been supplied during the process of supplying liquid through the liquid supply hole 60, and further it is possible to know how much liquid is remaining in the storage bottle 16, by using this graduated scale 62.

This graduated scale 62 may also be provided even when the liquid supply hole 60 is provided in the side wall surface 16*b* of the bottle 16, as in the second preferred embodiment described above, as a matter of course.

Although in the above described second and third preferred embodiments the plug 61 for the liquid supply hole 60 is made of elastic material having an H shaped cross section, in fact it is also possible to use a threaded plug 61, and to provide a thread also in the liquid supply hole 60 in the liquid storage bottle 16, so that said threaded plug 61 may be fitted into the hole 60 by screwing.

Thus, according to this bottle for the ultrasonic inhaler of this invention, since the liquid supply hole 60 having the plug 61 is provided in the vicinity of the nozzle fitting opening 2 so that the liquid may be supplied through this liquid supply hole 60 it is possible to supply liquid into the liquid storage bottle 16 without removing said liquid storage bottle 16 having the liquid supply nozzle 17 or the liquid supply unit 3 from the main body 5 of the ultrasonic inhaler 1, and the process of liquid supply or resupply is extremely simplified over the prior art, because there is no need to remove the liquid supply nozzle 17 every time the liquid is to be supplied into the liquid storage bottle 16. And also the possibility of improper mounting of the liquid supply nozzle 17 is eliminated. Furthermore, there is no worry for losing the liquid supply nozzle 17 because of removing it. Also, because one does not touch the liquid contact portion of the storage bottle 16 when supplying the liquid thereinto, the ultrasonic inhaler is very hygienic.

Although the present invention has been shown and described with reference to the preferred embodiments thereof, and in terms of the illustrative drawings, it should not be considered as limited thereby. Various possible modifications, omissions, and alterations could be conceived of by one skilled in the art to the form and the content of any particular embodiment, without departing from the scope of the present invention. Therefore it is desired that the scope of the present invention, and of the protection sought to be granted by Letters Patent, should be defined not by any of the perhaps purely fortuitous details of the shown preferred embodiments, or of the drawings, but solely by the scope of the appended claims, which follow.

What is claimed is:

1. An ultrasonic atomizer for atomizing a liquid comprising:

an oscillating member;

a means for vibrating said oscillating member at an ultrasonic frequency;

a bottle, with an opening, for storing the liquid to be atomized, said bottle disposed above said oscillating member when said atomizer is oriented for use; and a nozzle means fitted within said bottle opening for directing fluid downwardly from said bottle toward said oscillating member for atomization, said nozzle means having a tip portion extending from said bottle toward said oscillating member with a very narrow gap therebetween, said nozzle means having a fine liquid conducting groove means for leading liquid from said bottle downwardly to said tip portion by capillary action and gravitational action, and said nozzle means further having an air conducting groove means for introducing air from the outside of said bottle to the inside of said bottle, wherein the liquid to be atomized travels from the bottle, through the nozzle means to the vicinity of the oscillating member for atomization.

2. An ultrasonic atomizer according to claim 1, wherein said fine liquid conducting groove means is orientated in the longitudinal direction of said nozzle means.

3. An ultrasonic atomizer according to claim 2, wherein said air conducting groove means is orientated in the longitudinal direction of said nozzle means.

4. An ultrasonic atomizer according to claim 2, wherein said nozzle means is further formed with a liquid accumulation groove means substantially orientated in the circumferential direction of said nozzle means.

5. An ultrasonic atomizer according to claim 2, further comprising a tube member fitted between said nozzle means and said opening of said bottle, wherein said tube member serves for partly delimiting said fine liquid conducting groove means.

6. An ultrasonic atomizer according to claim 5, wherein said tube member is in the radially compressed state as fitted between said nozzle and said opening of said bottle.

7. An ultrasonic atomizer according to claim 1, further comprising a tube member fitted between said nozzle means and said opening of said bottle.

8. An ultrasonic atomizer according to claim 7, wherein said tube member is elastic.

9. An ultrasonic atomizer according to claim 8, wherein said tube member is in the radially compressed state as fitted between said nozzle means and said opening of said bottle.

10. An ultrasonic atomizer according to claim 1, wherein the portion of said bottle remote from said opening thereof is flexible.

11. An ultrasonic atomizer according to claim 1, wherein said bottle is flexible.

12. An ultrasonic atomizer according to claim 1, wherein said bottle is formed with a filling opening proximate to said opening thereof in which said nozzle is fitted.

13. An ultrasonic atomizer according to claim 12, further comprising a plug fitted into said filling opening of said bottle.

14. An ultrasonic atomizer according to claim 13, wherein said plug has a cross section generally resembling the letter "H.".

15. An ultrasonic atomizer according to claim 13 wherein said plug and said filling opening are both formed with threaded shapes, and are engaged together by their said threaded shapes.

16. An ultrasonic atomizer according to claim 12, wherein said filling opening of said bottle is formed substantially in a bottom planar portion of said bottle in which is also formed said said opening of said bottle in which said nozzle means is fitted.

17. An ultrasonic atomizer according to claim 12, wherein said filling opening of said bottle is formed substantially in a side planar portion of said bottle.

* * * * *